US007968709B2

(12) United States Patent
Tesconi et al.

(10) Patent No.: US 7,968,709 B2
(45) Date of Patent: Jun. 28, 2011

(54) PROCESS FOR PREPARING POLYMORPH FORM II OF TANAPROGET

(75) Inventors: Marc Sadler Tesconi, Monroe, NY (US); Mannching Sherry Ku, Thiells, NY (US); Yan Xu, New City, NY (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 12/792,978

(22) Filed: Jun. 3, 2010

(65) Prior Publication Data

US 2010/0267715 A1 Oct. 21, 2010

Related U.S. Application Data

(62) Division of application No. 11/412,015, filed on Apr. 26, 2006, now Pat. No. 7,759,341.

(60) Provisional application No. 60/675,737, filed on Apr. 28, 2005.

(51) Int. Cl.
*C07D 265/18* (2006.01)
(52) U.S. Cl. ........................................ 544/92
(58) Field of Classification Search ............ 544/92
See application file for complete search history.

(56) References Cited

U.S. PATENT DOCUMENTS

| 6,436,929 | B1 | 8/2002 | Zhang |
| 7,081,457 | B2 | 7/2006 | Zhang |
| 7,192,956 | B2 | 3/2007 | Fensome |
| 7,268,149 | B2 | 9/2007 | Fensome |
| 7,569,564 | B2 | 8/2009 | Zhang |
| 7,569,679 | B2 | 8/2009 | Shen |
| 2006/0246128 | A1 | 11/2006 | Nagi |
| 2006/0246135 | A1 | 11/2006 | Nagi |
| 2006/0247234 | A1 | 11/2006 | Nagi |
| 2006/0247236 | A1 | 11/2006 | Chatlapalli |
| 2006/0280800 | A1 | 12/2006 | Nagi |

FOREIGN PATENT DOCUMENTS

| WO | WO-00/66570 | 11/2000 |
| WO | WO-2005/104711 | 11/2005 |
| WO | WO-2005/105817 | 11/2005 |

OTHER PUBLICATIONS

Fensome, "Synthesis and Structure-Activity Relationship of Novel 6-Aryl-1,4-dihydrobenzo[d][1.3]oxazine-2-thiones as Progesterone Receptor Modulators Leading to the Potent and Selective Nonsteroidal Progesterone Receptor Agonists Tanaproget" Journal of Medicinal Chemistry, vol. 48, pp. 5092-5092 (Jul. 12, 2005).
Zhang, "Novel 6-Aryl-1,4-dihydrobenzo[d][1,3]oxazine-2-thiones as Potent, Selective, and Orally Active Nonsteroidal Progesterone Receptor Agonists", Bioorganic & Medicinal Chemistry Letters, vol. 13, pp. 1313-1316 (Apr. 7, 2003).
Winneker, "Nonsteroidal Progesterone Receptor Modulators: Structure Activity Relationships", Seminars in Reproductive Medicine, 23(1):46 (Feb. 2005).
Borka, "Crystal Polymorphism of Pharmaceuticals", Acta Pharmaceutica Jugoslavia, vol. 40, pp. 71-94, (1990).
Bapst, "Clinical Pharmacokinetics of Tanaproget, A Non-Steroidal Progesterone Receptor (PR) Agonist, in Healthy Cycling Women During 28 Days of Administration", American Society for Clinical Pharmacology and Therapeutics, Abstract PI-138, (Feb. 2005), p. 44.
Crabtree, "Development of a Mouse Model of Mammary Gland Versus Uterus Tissue Selectivity Using Estrogen- and Progesterone-Regulated Gene Markers", Journal of Steroid Biochemistry & Molecular Biology, vol. 101, (Sep. 2006; e-published Aug. 22, 2006), pp. 11-21.
Bapst, "Pharmacokinetics and Safety of Tanaproget, a Nonsteroidal Progesterone Receptor Agonist, in Healthy Woman", Contraception, vol. 74 (Nov. 2006; e-published Sep. 15, 2006), pp. 414-418.
Bruner-Tran, "Down-Regulation of Endometrial Matrix Metalloproteinase-3 and—7 Expression in Vitro and Therapeutic Regression of Experimental Endometriosis in Vivo by a Novel Nonsteroidal Progesterone Receptor Agonist, Tanaproget", Journal of Clinical Endocrinology & Metabolism, vol. 91, No. 4 (Apr. 2006; e-published Jan. 17, 2006), pp. 1554-1560.
Rasenack, "Microcrystals for Dissolution Rate Enhancement of Poorly Water-Soluble Drugs", International Journal of Pharmaceutics, vol. 254, pp. 137-145 (Mar. 26, 2003).
International Search Report issued in International Patent Application No. PCT/US06/015852 (Oct. 2, 2006).
English translation of an Office Action issued in Chinese Patent Application No. 200680014221.8 (dated Dec. 4, 2009).
Office Action issued in U.S. Appl. No. 11/412,015 (Nov. 12, 2008).
Applicants' Response to the Office Action issued in U.S. Appl. No. 11/412,015 (Nov. 12, 2008).
Office Action issued in U.S. Appl. No. 11/412,015 (Apr. 2, 2009).
Applicants' Response to the Office Action issued in U.S. Appl. No. 11/412,015 (Apr. 2, 2009).
Office Action issued in U.S. Appl. No. 11/412,015 (Nov. 27, 2009).
Applicants' Response to the Office Action issued in U.S. Appl. No. 11/412,015 (Nov. 27, 2009).
Office Action issued in U.S. Appl. No. 11/412,016 (Nov. 12, 2008).

(Continued)

*Primary Examiner* — James O Wilson
*Assistant Examiner* — Brian McDowell
(74) *Attorney, Agent, or Firm* — Howson & Howson LLP

(57) ABSTRACT

Tanaproget polymorph Form II, processes for preparing tanaproget polymorph Form II, pharmaceutical compositions including tanaproget polymorph Form II, micronized tanaproget polymorph Form II, and processes for converting Form II to tanaproget Form I are provided. Also provided are methods of contraception, hormone replacement therapy, stimulation of food intake and treating or preventing uterine myometrial fibroids, benign prostatic hypertrophy, benign and malignant neoplastic disease, dysfunctional bleeding, uterine leiomyomata, endometriosis, polycystic ovary syndrome, or carcinomas and adenocarcinomas comprising administering polymorph Form II to a mammalian subject.

6 Claims, 2 Drawing Sheets

OTHER PUBLICATIONS

Applicants' Response to the Office Action issued in U.S. Appl. No. 11/412,016 (Nov. 12, 2008).
Office Action issued in U.S. Appl. No. 11/412,016 (Aug. 19, 2009).
Applicants' Response to the Office Action issued in U.S. Appl. No. 11/412,016 (Aug. 19, 2009).
Office Action issued in U.S. Appl. No. 11/412,016 (Apr. 29, 2010).
Applicants' Response to the Office Action issued in U.S. Appl. No. 11/412,016 (Apr. 29, 2010).
Office Action issued in U.S. Appl. No. 11/411,523 (Oct. 1, 2008).
Applicants' Response to the Office Action issued in U.S. Appl. No. 11/411,523 (Oct. 1, 2008).
Office Action issued in U.S. Appl. No. 11/411,523 (Mar. 4, 2009).
Applicants' Response to the Office Action issued in U.S. Appl. No. 11/411,523 (Mar. 4, 2009).
Correspondence from the Mexican associate regarding an Office Action issued on Jul. 12, 2010 in Mexican Patent Application No. MX/a/2007/013469.

PROCESS FOR PREPARING POLYMORPH FORM II OF TANAPROGET

CROSS-REFERENCE TO RELATED APPLICATIONS

This application is a divisional of U.S. patent application Ser. No. 11/412,015, filed Apr. 26, 2006, which claims the benefit of the priority of U.S. Provisional Patent Application No. 60/675,737, filed Apr. 28, 2005. These priority applications are hereby incorporated by reference.

BACKGROUND OF THE INVENTION

A novel tanaproget polymorph Form II and compositions containing the same are provided as described herein.

Intracellular receptors (IR) form a class of structurally related gene regulators known as "ligand dependent transcription factors". The steroid receptor family is a subset of the IR family, including progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as ligands. Once a ligand is present in the fluid surrounding a cell, it passes through the membrane via passive diffusion, and binds to the IR to create a receptor/ligand complex. This complex binds to specific gene promoters present in the cell's DNA. Once bound to the DNA the complex modulates the production of mRNA and protein encoded by that gene.

A compound that binds to an IR and mimics the action of the natural hormone is termed an agonist, whilst a compound which inhibits the effect of the hormone is an antagonist.

PR agonists (natural and synthetic) are known to play an important role in the health of women. PR agonists are used in birth control compositions, typically in the presence of an ER agonist, alternatively they may be used in conjunction with a PR antagonist. ER agonists are used to treat the symptoms of menopause, but have been associated with a proliferative effect on the uterus which can lead to an increased risk of uterine cancers. Co-administration of a PR agonist reduces/ablates that risk.

Tanaproget, 5-(4,4-dimethyl-2-thioxo-1,4-dihydro-2H-3,1-benzoxazin-6-yl)-1H-pyrrole-2-carbonitrile, is a progesterone receptor modulator and is effective in contraception, hormone replacement therapy, and treating carcinomas and adenocarcinomas, dysfunctional bleeding, uterine leiomyomata, endometriosis, and polycystic ovary syndrome.

What is needed in the art are alternate forms of tanaproget.

SUMMARY OF THE INVENTION

In one aspect, tanaproget polymorph Form II is provided.

In a further aspect, micronized tanaproget polymorph Form II is provided.

In another aspect, a process for preparing tanaproget polymorph Form II is provided.

In still a further aspect, a pharmaceutical composition containing tanaproget polymorph Form II is provided.

In yet another aspect, a kit containing tanaproget polymorph Form II is provided.

In a further aspect, a method of preparing a pharmaceutical composition containing tanaproget polymorph Form II is provided.

In yet another aspect, a process for preparing tanaproget polymorph Form I from tanaproget polymorph Form II is provided.

In a further aspect, methods of contraception, hormone replacement therapy, and stimulation of food intake using tanaproget polymorph Form II are provided.

In still another aspect, methods of treating and preventing uterine myometrial fibroids, benign prostatic hypertrophy, benign and malignant neoplastic disease, dysfunctional bleeding, uterine leiomyomata, endometriosis, polycystic ovary syndrome, and carcinomas and adenocarcinomas of the pituitary, endometrium, kidney, ovary, breast, colon, and prostate and other hormone-dependent tumors using tanaproget polymorph Form II are provided.

Other aspects and advantages of the present invention are described further in the following detailed description of the preferred embodiments thereof.

DETAILED DESCRIPTION OF THE INVENTION

Figure 1:
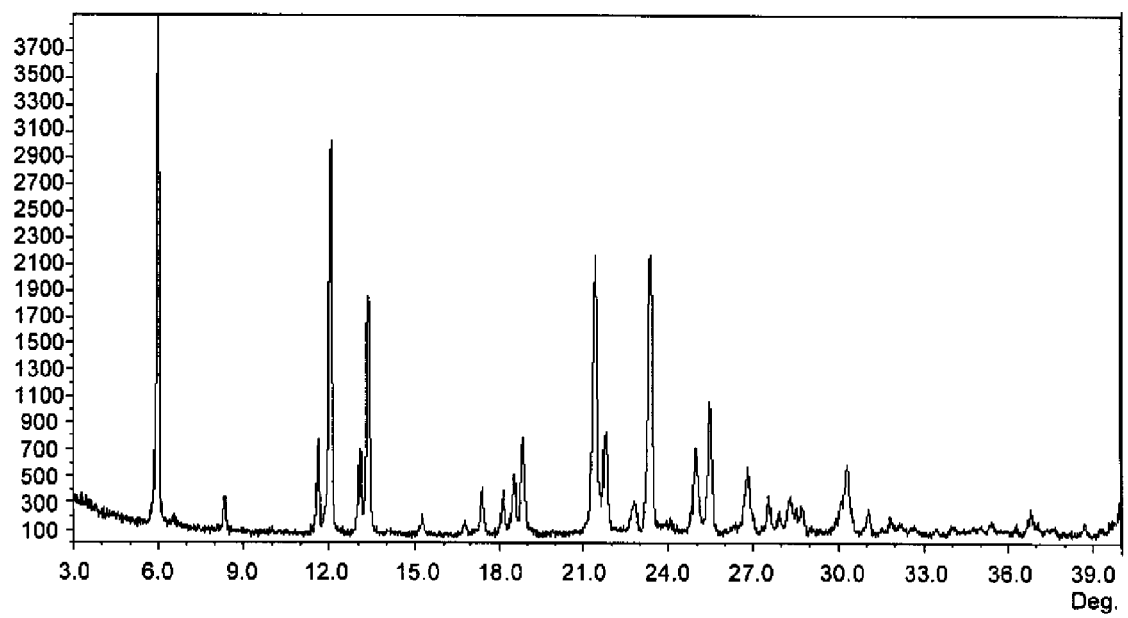
FIG. 1 provides the X-ray diffraction pattern for tanaproget polymorph Form II.

A novel polymorph of tanaproget, denoted herein as Form II, is described. Form II differs from Form I in the structure of the crystal lattice of tanaproget Form I and in its chemical properties.

As used herein, "tanaproget" or "Form I" refers to tanaproget, i.e., 5-(4,4-dimethyl-2-thioxo-1,4-dihydro-2H-3,1-benzoxazin-6-yl)-1-methyl-1H-pyrrole-2-carbonitrile, regardless of particle size or purity. Tanaproget can be purified according to the procedure set forth in US Patent Application Publication No. US 2005-0272702 A1 which is hereby incorporated by reference.

In another embodiment, tanaproget Form I is purified by recrystallization. Desirably, the tanaproget is recrystallized from acetone and water. More desirably, the tanaproget is dissolved in acetone, the acetone solution heated, water added to the heated acetone solution, and the acetone/water solution cooled to provide purified tanaproget. This purification specifically includes dissolving crude tanaproget in acetone and heating the solution to about 45 to about 51° C. After circulating the heated solution through a carbon filter for at least about 4 hours, the filtered solution was concentrated using procedures known to those of skill in the art. After adding water to the concentrated solution, desirably at a rate which does not cool the refluxing acetone solution, the acetone/water solution is cooled to about −6 to about 0° C. Desirably, the acetone/water solution is cooled at a rate of less than about 0.5° C./minute. After holding the batch at the reduced temperature for at least about 3 hours, the precipitated, purified tanaproget is collected using filtration. The collected solid is washed with a water/acetone mixture, desirably washing the solid twice with a 1:1 water/acetone mixture. The washed purified tanaproget is then dried at less than 35° C. for about 4 hours. Further drying at less than about 50° C. is performed to remove residual acetone/water as measured by spectroscopic methods.

"Tanaproget" or "Form I" also refers to both non-micronized and micronized forms of the same. Micronization of tanaproget is typically accomplished under nitrogen and conventional micronizing techniques, for example with a Trost or jet mill, applied to non-micronized tanaproget. One method of preparation of non-micronized tanaproget is described in U.S. Pat. No. 6,436,929 and another is generally described in US Patent Application Publication No. US-2005-0272702-A1, which are hereby incorporated by reference. Desirably, the non-micronized tanaproget is prepared as described in US Patent Application Publication No. US-2005-0272702-A1. However, the novel polymorph Form II is not limited to the method by which the non-micronized tanaproget is produced.

Micronized tanaproget prepared or used typically has a particle size of less than about 20 μm, and desirably less than about 15 μm. Desirably, 90% of the particles are less than or equal to about 20 μm and 50% are less than or equal to about 15 μm, and more desirably less than about 10 μm, as determined by the Malvern method, which is readily understood by one of skill in the art. More desirably, most of the particles are less than or equal to about 10 μm.

A. Spectroscopic Identification of Form II

Tanaproget Form I has a differential scanning calorimetry thermogram which includes an endotherm peak of about 230° C. Further, the X-ray diffraction (XRD) pattern contains peaks at 2θ of about 6.6°, 10.3°, 14.4°, 19.8°, 23.8°, 26.3°, and 29.1°.

Figure 2:
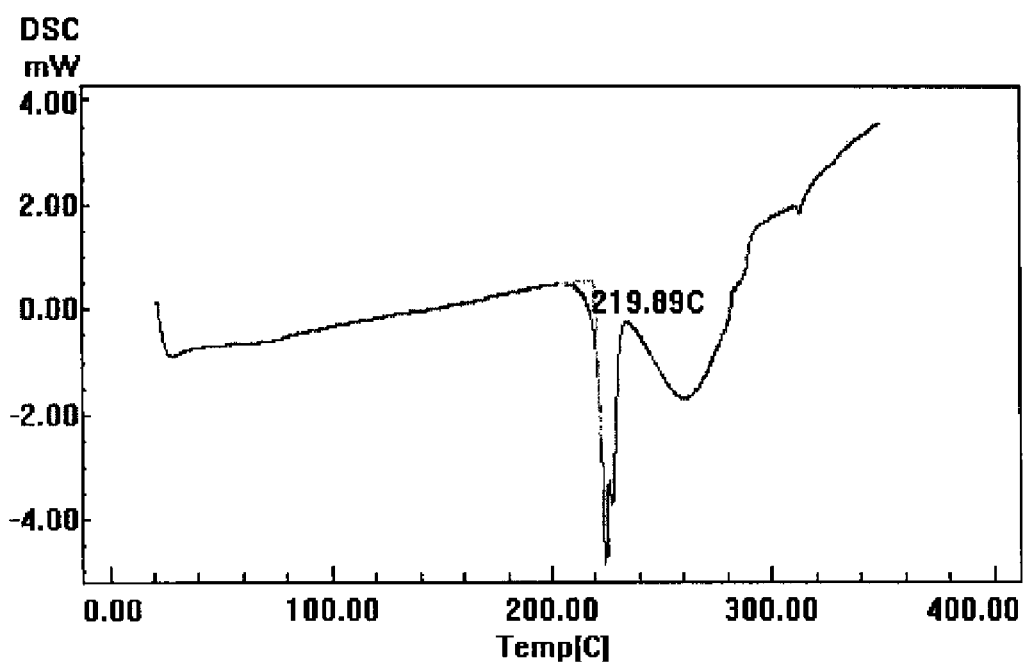
FIG. 2 provides the differential scanning calorimetry thermogram for tanaproget polymorph Form II.

The XRD pattern of tanaproget polymorph Form II differs from the XRD pattern of Form I and includes peaks at 2θ of about 6.0°, 8.3°, 12.0°, 21.4°, and 23.4°. See, FIG. 1. The differential scanning calorimetry (DSC) thermogram of Form II also differs from the DSC thermogram of Form I and has a $T_{onset}$ of about 219° C. See, FIG. 2.

B. Preparing the Form II Tanaproget Polymorph

The Form II tanaproget polymorph is typically prepared by recrystallizing non-micronized or micronized tanaproget Form I from selected solvent systems. Preferred solvent systems for use in preparing Form II include, without limitation, the methylene chloride and pentane solvent system; the acetonitrile and water solvent system; and the methanol and water solvent system.

(i) The Methylene Chloride/Pentane Solvent System

In one embodiment, Form II is prepared using the methylene chloride/pentane solvent system. In this process, Form I is dissolved in methylene chloride and optionally warmed to temperatures of about reflux temperatures. The methylene chloride solution is then optionally concentrated and pentane is added. The pentane can be layered onto the methylene chloride solution and mixed therein or mixed directly into the methylene chloride solution. The methylene chloride/pentane solution is thereby cooled, desirably to about 20° C. By doing so, tanaproget polymorph Form II precipitates from the methylene chloride/pentane solution and is collected using techniques known in the art. The collected Form II can then be dried using techniques known in the art and include the use of reduced pressures and elevated temperatures, among other techniques.

(ii) The Acetonitrile/Water Solvent System

In another embodiment, Form II is prepared using the acetonitrile/water solvent system. In this process, Form I is dissolved in acetonitrile, optionally warmed to temperatures of about reflux temperatures. The acetonitrile solution is then optionally concentrated and water is added. The water can be layered onto the acetonitrile solution and mixed therein or mixed directly into the acetonitrile solution. The acetonitrile/water solution is thereby cooled, desirably to room temperature or below. By doing so, tanaproget polymorph Form II precipitates from the acetonitrile/water solution and is collected using techniques known in the art. The collected Form II can then be dried using techniques known in the art and include the use of reduced pressures and elevated temperatures, among other techniques.

(iii) The Methanol/Water Solvent System

In a further embodiment, Form II is prepared using the methanol/water solvent system. In this process, Form I is dissolved in methanol, optionally warmed to temperatures of about reflux temperatures. The methanol solution is then optionally concentrated and water is added. The water can be layered onto the methanol solution and mixed therein or mixed directly into the methanol solution. The methanol/water solution is thereby cooled, desirably to room temperature or below. By doing so, tanaproget polymorph Form II precipitates from the methanol/water solution and is collected using techniques known in the art. The collected Form II can then be dried using techniques known in the art and include the use of reduced pressures and elevated temperatures, among other techniques.

C. Micronized Tanaproget Form II

Tanaproget Form II can be micronized under nitrogen and conventional micronizing techniques, for example with a Trost or jet mill, as discussed above for micronized tanaproget Form I.

Micronized tanaproget Form II typically has a median particle size of less than about 20 μm, desirably less than about 15 μm, and more desirably less than about 10 μm. Specifically, 90% of the particles are less than or equal to about 20 μm and 50% are less than or equal to about 15 μm as determined by the Malvern method, which is readily understood by one of skill in the art.

In one embodiment, micronized 5-(4,4-dimethyl-2-thioxo-1,4-dihydro-2H-3,1-benzoxazin-6-yl)-1-methyl-1H-pyrrole-2-carbonitrile Form II having a particle size less than about 20 μm is provided.

D. Compositions Containing the Form II Tanaproget Polymorph

Also provided are compositions, desirably pharmaceutical compositions, containing tanaproget polymorph Form II alone or in combination with Form I. The compositions typically contain a pharmaceutically acceptable carrier, but can also contain other suitable components. Typically, the additional components are inert and do not interfere with the function of the required components of the compositions. The compositions can thereby further include other adjuvants, syrups, elixirs, diluents, binders, lubricants, surfactants, granulating agents, disintegrating agents, emollients, metal chelators, pH adjustors, surfactants, fillers, disintegrants, and combinations thereof, among others.

Adjuvants can include, without limitation, flavoring agents, coloring agents, preservatives, and supplemental antioxidants, which can include vitamin E, ascorbic acid, butylated hydroxytoluene (BHT) and butylated hydroxyanisole (BHA).

Binders can include, without limitation, povidone, cellulose, methylcellulose, hydroxymethylcellulose, carboxymethylcellulose calcium, carboxymethylcellulose sodium, hydroxypropylcellulose, hydroxypropylmethylcellulose phthalate, noncrystalline cellulose, polypropylpyrrolidone, polyvinylpyrrolidone (povidone, PVP), gelatin, gum arabic and acacia, polyethylene glycols, starch, sugars such as sucrose, kaolin, dextrose, and lactose, cholesterol, tragacanth, stearic acid, gelatin, casein, lecithin (phosphatides), cetostearyl alcohol, cetyl alcohol, cetyl esters wax, dextrates, dextrin, glyceryl monooleate, glyceryl monostearate, glyceryl palmitostearate, polyoxyethylene alkyl ethers, polyoxyethylene castor oil derivatives, polyoxyethylene stearates, polyvinyl alcohol, and gelatin, among others. In one embodiment, the binder is povidone.

Lubricants can include light anhydrous silicic acid, talc, stearic acid, sodium lauryl sulfate, magnesium stearate and sodium stearyl furamate, among others. In one embodiment, the lubricant is magnesium stearate.

Granulating agents can include, without limitation, silicon dioxide, starch, calcium carbonate, pectin, crospovidone, and polyplasdone, among others.

Disintegrating agents or disintegrants can include starch, carboxymethylcellulose, substituted hydroxypropylcellulose, sodium bicarbonate, calcium phosphate, calcium citrate, sodium starch glycolate, pregelatinized starch or crospovidone, among others.

Emollients can include, without limitation, stearyl alcohol, mink oil, cetyl alcohol, oleyl alcohol, isopropyl laurate, polyethylene glycol, olive oil, petroleum jelly, palmitic acid, oleic acid, and myristyl myristate.

Surfactants can include polysorbates, sorbitan esters, poloxamer, or sodium lauryl sulfate. In one embodiment, the surfactant is sodium lauryl sulfate.

Metal chelators can include physiologically acceptable chelating agents including edetic acid, malic acid, or fumaric acid. In one embodiment, the metal chelator is edetic acid.

pH adjusters can also be utilized to adjust the pH of a solution containing tanaproget to about 4 to about 6. In one embodiment, the pH of a solution containing tanaproget is adjusted to a pH of about 4.6. pH adjustors can include physiologically acceptable agents including citric acid, ascorbic acid, fumaric acid, or malic acid, and salts thereof. In one embodiment, the pH adjuster is citric acid.

Additional fillers that can be used in the composition include mannitol, calcium phosphate, pregelatinized starch, or sucrose.

E. Methods of Using the Form II Tanaproget Polymorph

Further provided are methods of delivering tanaproget polymorph Form II to a patient, where the method includes administering Form II.

The dosage requirements of Form II may vary based on the severity of the symptoms presented and the particular subject being treated. Treatment can be initiated with small dosages less than the optimum dose of Form II. Thereafter the dosage is increased until the optimum effect under the circumstances is reached. Precise dosages will be determined by the administering physician based on experience with the individual subject treated. In general, Form II is most desirably administered at a concentration that will generally afford effective results without causing any unacceptable harmful or deleterious side effects. For example, an effective amount of Form II is generally, e.g., about 0.05 mg to about 1 mg, about 0.05 mg to about 0.3 mg, about 0.05 mg, about 0.075 mg, about 0.1 mg, about 0.15 mg, about 0.2 mg, or about 0.3 mg.

Form II is therefore useful in contraception and hormone replacement therapy. Form II is also useful in contraception and the treatment and/or prevention of uterine myometrial fibroids, benign prostatic hypertrophy, benign and malignant neoplastic disease, dysfunctional bleeding, uterine leiomyomata, endometriosis, polycystic ovary syndrome, and carcinomas and adenocarcinomas of the pituitary, endometrium, kidney, ovary, breast, colon, and prostate and other hormone-dependent tumors. Additional uses of Form II include stimulation of food intake.

Tanaproget polymorph Form II can be formulated in any form suitable for the desired route of delivery using a pharmaceutically effective amount of Form II. For example, Form II can be delivered by a route such as oral, dermal, transdermal, intrabronchial, intranasal, intravenous, intramuscular, subcutaneous, parenteral, intraperitoneal, intranasal, vaginal, rectal, sublingual, intracranial, epidural, intratracheal, or by sustained release. Desirably, delivery is oral.

For example, Form II may be formulated for administration orally in such forms as tablets, capsules, microcapsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like. The preferred pharmaceutical compositions from the standpoint of ease of preparation and administration are solid compositions, particularly tablets and hard-filled or liquid-filled capsules.

Form II may also be administered parenterally or intraperitoneally. Solutions or suspensions of Form II can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms. Typically, such sterile injectable solutions or suspensions contain from about 0.05 to 5% suspending agent in an isotonic medium. Such pharmaceutical preparations may contain, for example, from about 25 to about 90% of the active ingredient in combination with the carrier, more usually between about 5% and 60% by weight.

In another embodiment, Form II is delivered intravenously, intramuscularly, subcutaneously, parenterally and intraperitoneally in the form of sterile injectable solutions, suspensions, dispersions, and powders which are fluid to the extent that easy syringe ability exits. Such injectable compositions are sterile, stable under conditions of manufacture and storage, and free of the contaminating action of microorganisms such as bacteria and fungi.

The carrier can be a solvent or dispersion medium containing, for example, water, ethanol (e.g., glycerol, propylene glycol and liquid polyethylene glycol), oils, and mixtures thereof. Desirably the liquid carrier is water. In one embodiment, the oil is vegetable oil. Optionally, the liquid carrier contains a suspending agent. In another embodiment, the liquid carrier is an isotonic medium and contains 0.05 to about 5% suspending agent.

In a further embodiment, Form II is delivered rectally in the form of a conventional suppository.

In another embodiment, Form II is delivered vaginally in the form of a conventional suppository, cream, gel, ring, or coated intrauterine device (IUD).

In yet another embodiment, Form II is delivered intranasally or intrabronchially in the form of an aerosol.

In a further embodiment, Form II is delivered transdermally or by sustained release through the use of a transdermal patch containing Form II and an optional carrier that is inert to Form II, is nontoxic to the skin, and allows for delivery of Form II for systemic absorption into the blood stream. Such a carrier can be a cream, ointment, paste, gel, or occlusive device. The creams and ointments can be viscous liquid or semisolid emulsions. Pastes include absorptive powders dispersed in petroleum or hydrophilic petroleum. Further, a variety of occlusive devices can be utilized to release Form II into the blood stream and include semi-permeable membranes covering a reservoir contain the active reagents, or a matrix containing the reactive reagents.

The use of sustained delivery devices can be desirable, in order to avoid the necessity for the patient to take medications on a daily basis. The term "sustained delivery" is used herein to refer to delaying the release of an active agent, i.e., tanaproget polymorph Form II, until after placement in a delivery environment, followed by a sustained release of the agent at a later time. A number of sustained delivery devices are known in the art and include hydrogels (U.S. Pat. Nos. 5,266,325;

4,959,217; 5,292,515), osmotic pumps (U.S. Pat. Nos. 4,295,987 and 5,273,752 and European Patent No. 314,206, among others); hydrophobic membrane materials, such as ethylenemethacrylate (EMA) and ethylenevinylacetate (EVA); bioresorbable polymer systems (International Patent Publication No. WO 98/44964 and U.S. Pat. Nos. 5,756,127 and 5,854,388); and other bioresorbable implant devices composed of, for example, polyesters, polyanhydrides, or lactic acid/glycolic acid copolymers (U.S. Pat. No. 5,817,343). For use in such sustained delivery devices, Form II can be formulated as described herein. See, U.S. Pat. Nos. 3,845,770; 3,916,899; 3,536,809; 3,598,123; and 4,008,719.

Desirably, Form II is formed into a suitable dosing unit for delivery to a patient. Suitable dosing units include oral dosing units, such as a directly compressible tablets, capsules, powders, suspensions, microcapsules, dispersible powders, granules, suspensions, syrups, elixirs, and aerosols. Desirably, Form II is compressed into a tablet, which is optionally added to a capsule, or Form II is added directly to a capsule. Form II can also be formulated for delivery by other suitable routes. These dosing units are readily prepared using the methods described herein and those known to those of skill in the art.

Solid forms, including tablets, caplets, and capsules containing tanaproget Form II can be formed by dry blending tanaproget with the components described above. In one embodiment, the capsules utilized include hydroxypropyl methylcellulose, hypromellose capsule, or a hard shell gelatin capsule. The tablets or caplets that contain tanaproget are optionally film-coated. Suitable film-coatings are known to those of skill in the art. For example, the film-coating can be selected from among polymers such as hydroxypropylmethylcellulose, ethyl cellulose, polyvinyl alcohol, and combinations thereof.

A pharmaceutically effective amount of Form II can vary depending on the other components of the composition being delivered, mode of delivery, severity of the condition being treated, the patient's agent and weight, and any other active ingredients used in the composition. The dosing regimen can also be adjusted to provide the optimal therapeutic response. Several divided doses can be delivered daily, e.g., in divided doses 2 to 4 times a day, or a single dose can be delivered. The dose can however be proportionally reduced or increased as indicated by the exigencies of the therapeutic situation. In one embodiment, the delivery is on a daily, weekly, or monthly basis. In another embodiment, the delivery is on a daily delivery. However, daily dosages can be lowered or raised based on the periodic delivery.

It is contemplated that when Form II is used for contraception or hormone replacement therapy, it can be administered in conjunction with one or more other progesterone receptor agonists, estrogen receptor agonists, progesterone receptor antagonists, and selective estrogen receptor modulators, among others.

When utilized for treating neoplastic disease, carcinomas, and adenocarcinomas, Form II can be administered in conjunction with one or more chemotherapeutic agents which can readily be selected by one of skill in the art.

F. Kits Containing Tanaproget Polymorph Form II

Also provided are kits or packages containing tanaproget polymorph Form II. Kits can include Form II or in combination with Form I and a carrier suitable for administration to a mammalian subject as discussed above. Typically, the tablets or capsules are packaged in blister packs, and desirably Ultrx™ 2000 blister packs The kits or packages containing Form II are designed for use in the regimens described herein. These kits are desirably designed for daily oral delivery over 21-day, 28-day, 30-day, or 31-day cycles, among others, and more desirably for one oral delivery per day. When Form II is to be delivered continuously, a package or kit can include Form II in each tablet. When Form II is to be delivered with periodic discontinuation, a package or kit can include placebos on those days when Form II is not delivered.

Additional components may be co-administered with Form II and include progestational agents, estrogens, and selective estrogen receptor modulators.

The kits are also desirably organized to indicate a single oral formulation or combination of oral formulations to be taken on each day of the cycle, desirably including oral tablets to be taken on each of the days specified, and more desirably one oral tablet will contain each of the combined daily dosages indicated.

In one embodiment, a kit can include a single phase of a daily dosage of Form II over a 21-day, 28-day, 30-day, or 31-day cycle. Alternatively, a kit can include a single phase of a daily dosage of Form II over the first 21 days of a 28-day, 30-day, or 31-day cycle. A kit can also include a single phase of a daily dosage of Form II over the first 28 days of a 30-day or 31-day cycle.

In a further embodiment, a kit can include a single combined phase of a daily dosage of Form II and a progestational agent over a 21-day, 28-day, 30-day, or 31-day cycle. Alternatively, a kit can include a single combined phase of a daily dosage of Form II and a progestational agent over the first 21 days of a 28-day, 30-day, or 31-day cycle. A kit can also include a single combined phase of a daily dosage of Form II and a progestational agent over the first 28 days of a 30-day or 31-day cycle.

In another embodiment, a 28-day kit can include a first phase of from 14 to 28 daily dosage units of Form II; a second phase of from 1 to 11 daily dosage units of a progestational agent; and, optionally, a third phase of an orally and pharmaceutically acceptable placebo for the remaining days of the cycle.

In yet a further embodiment, a 28-day kit can include a first phase of from 14 to 21 daily dosage units of Form II; a second phase of from 1 to 11 daily dosage units of a progestational agent; and, optionally, a third phase of an orally and pharmaceutically acceptable placebo for the remaining days of the cycle.

In another embodiment, a 28-day kit can include a first phase of from 18 to 21 daily dosage units of Form II; a second phase of from 1 to 7 daily dose units of a progestational agent; and, optionally, an orally and pharmaceutically acceptable placebo for each of the remaining 0 to 9 days in the 28-day cycle.

In yet a further embodiment, a 28-day kit can include a first phase of 21 daily dosage units of Form II; a second phase of 3 daily dosage units for days 22 to 24 of a progestational agent; and, optionally, a third phase of 4 daily units of an orally and pharmaceutically acceptable placebo for each of days 25 to 28.

In another embodiment, a 28-day kit can include a first phase of from 14 to 21 daily dosage units of a progestational agent equal in progestational activity to about 35 to about 150 µg levonorgestrel, a second phase of from 1 to 11 daily dosage units of Form II; and optionally, a third phase of an orally and pharmaceutically acceptable placebo for the remaining days of the cycle in which no antiprogestin, progestin or estrogen is administered.

In a further embodiment, a 28-day kit can include a first phase of from 14 to 21 daily dosage units of a progestational agent equal in progestational activity to about 35 to about 100 µg levonorgestrel; a second phase of from 1 to 11 daily dosage units of Form II; and optionally, a third phase of an orally and pharmaceutically acceptable placebo for the remaining days of the cycle in which no antiprogestin, progestin or estrogen is administered.

Desirably, the daily dosage of Form II remains fixed in each particular phase in which it is delivered. It is further preferable that the daily dose units described are to be delivered in the order described, with the first phase followed in order by the second and third phases. To help facilitate compliance with each regimen, it is also preferred that the kits contain the placebo described for the final days of the cycle.

A number of packages or kits are known in the art for the use in dispensing pharmaceutical agents for oral use. Desirably, the package has indicators for each day of the 28-day cycle, and more desirably is a labeled blister package, dial dispenser package, or bottle.

The kit can further contain instructions for administering Form II.

G. Process for Converting Form II Tanaproget Polymorph to Form I

Also provided are processes for preparing tanaproget Form I from tanaproget polymorph Form II. Typically, Form II is converted to Form I via crystallization from a solvent system or directly from Form II without the use of a solvent.

In one embodiment, Form II is converted to Form I by combining Form II with acetone and water, desirably a 1:1 ratio of acetone to water. Form II is mixed with the acetone/water solution for a time that is sufficient to convert Form II to Form I. Typically, conversion of Form II to Form I occurs as Form II dissolves and Form I is recrystallized. The conversion can readily be monitored using XRD and DSC and, specifically, by monitoring the presence of the Form II XRD peaks and DSC endotherms. Complete conversion is noted by an absence of Form II XRD peaks and DSC endotherms.

Form I can precipitate from the acetone/water solvent in about 1, 2, 3, 4, 5, 6, or 6 days. Typically, Form I precipitates from the acetone/water solution, after about 1 week, and is collected using techniques known to those of skill in the art. However, conversion to Form I can be complete in less than 1 week or even less than 1 day depending on the conditions utilized during the conversion and any environmental factors present at the time of conversion.

In another embodiment, tanaproget polymorph Form II is converted to tanaproget Form I without the use of a solvent. Typically, Form II is first heated to its melting point, typically to about 219 to about 229° C., more desirably about 219 to about 216° C. Heating can be accomplished using a variety of techniques including, without limitation, hot stage microscopy. Once the Form II has melted, the liquid sample is typically maintained at about 219° C. to about 229° C. to promote crystallization of the Form I tanaproget polymorph. Form I is then collected using techniques known to those of skill in the art.

If crystallization to Form I does not occur between 219° C. and 229° C. within an acceptable period of time, the sample is slowly cooled below 219° C. until crystallization does occur.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

Preparation of Tanaproget Form II Polymorph from Tanaproget Form I Using Methylene Chloride/Pentane Tanaproget Form I polymorph (6.8 g) was dissolved in methylene chloride (100 mL) at 29° C. After cooling the solution to 20° C., pentane (150 mL) was added dropwise to the solution to give a suspension. The suspension was then filtered and the filter cake dried to give Tanaproget Form II polymorph (6.1 g).

Example 2

Preparation of Tanaproget Form II Polymorph from Tanaproget Form I Using Acetonitrile/Water Tanaproget Form I polymorph (73.9 mg) was dissolved in acetonitrile (2 mL) at 55° C. Water (about 1 mL) was then added dropwise to the acetonitrile solution. The suspension was maintained at room temperature overnight and then at 4° C. for 2 days. The sample was centrifuged and crystallized Tanaproget Form II polymorph (about 15 mg) was recovered and air dried.

Example 3

Preparation of Tanaproget Form I Polymorph from Tanaproget Form II

Tanaproget polymorph Form II (117.5 mg) was weighed into a 4 mL scintillation vial. Water (1 mL) and acetone (1 mL) were added and the slurry stirred for 5 days at room temperature. The sample was then centrifuged and the recovered solid was dried under vacuum for 2 days at room temperature to give Tanaproget Polymorph Form I. XRD and DSC analysis indicated a complete conversion to Form I.

Example 4

Preparation of Tanaproget Form II Polymorph from Tanaproget Form I Using Methanol/Water Tanaproget Form I polymorph is dissolved in methanol. Water is then added dropwise to the methanol solution. The suspension is maintained at room temperature overnight and then at reduced temperatures 4° C. for 2 days. The sample is centrifuged and crystallized Tanaproget Form II polymorph is recovered and air dried.

Example 5

Preparation of Tanaproget Form I Polymorph from Tanaproget Form II Using Heat

A sample of the Form II tanaproget polymorph is heated to a temperature of about 219° C. and about 229° C. heat until the entire sample is melted. Once a liquid forms, the temperature is maintained between about 219° C. and about 229° C. and crystallization to Form I tanaproget polymorph occurs. The sample is optionally cooled to below 219° C. to further crystallize the Form I tanaproget polymorph.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

We claim:

1. A process for preparing polymorph Form II of tanaproget, said process comprising recrystallizing tanaproget Form I from (i) methylene chloride and pentane; (ii) acetonitrile and water; or (iii) methanol and water;
   wherein the X-ray diffraction peak pattern for said polymorph Form II of tanaproget comprises peaks at 2θ of about 6.0°, 8.3°, 12.0°, 21.4°, and 23.4° and the X-ray diffraction peak pattern for said tanaproget Form I comprises peaks at 2θ of about 6.6°, 10.3°, 14.4°, 19.8°, 23.8°, 26.3°, and 29.1°.

2. The process according to claim 1, wherein said tanaproget Form I is recrystallized from (i) and said process comprises:
   (a) dissolving tanaproget Form I in methylene chloride;
   (b) heating the methylene chloride solution of step (a);
   (c) combining pentane with the product of step (b);
   (d) cooling the product of step (c) to 20° C.; and
   (e) collecting the polymorph tanaproget Form II.

3. The process according to claim 1, wherein said tanaproget Form I is recrystallized from (ii) and said process comprises:
   (a) dissolving tanaproget Form I in acetonitrile;
   (b) heating the acetonitrile solution of step (a);
   (c) combining water with the product of step (b);
   (d) cooling the product of step (c) to room temperature; and
   (e) collecting the polymorph tanaproget Form II.

4. The process according to claim 1, wherein said tanaproget Form I is recrystallized from (iii) and said process comprises:
   (a) dissolving tanaproget Form I in methanol;
   (b) heating the methanol solution of step (a);
   (c) combining water with the product of step (b); and
   (d) collecting the polymorph tanaproget Form II.

5. The process according to claim 1, wherein said polymorph Form II of tanaproget has
   a differential scanning calorimetry thermogram lacking an endotherm peak of about 230° C.

6. The process according to claim 1, wherein said polymorph Form II of tanaproget has
   a differential scanning calorimetry thermogram having a $T_{onset}$ of about 219° C.

* * * * *